United States Patent
Mifsud

[11] Patent Number: 6,015,412
[45] Date of Patent: Jan. 18, 2000

[54] CUTTING DEVICE

[75] Inventor: Simon Mifsud, Harrogate, United Kingdom

[73] Assignee: Atlantech Medical Devices Limited, North Yorkshire, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/003,340

[22] Filed: Jan. 6, 1998

[30] Foreign Application Priority Data

Jan. 8, 1997 [GB] United Kingdom .................. 9700236
Sep. 12, 1997 [GB] United Kingdom .................. 9719317

[51] Int. Cl.[7] .......................... A61B 17/56; A61B 17/32
[52] U.S. Cl. ............................ 606/83; 606/174
[58] Field of Search ................. 606/79, 83, 167, 606/174, 175, 184, 207, 208; 188/376; 604/22; 128/751

[56] References Cited

U.S. PATENT DOCUMENTS

| | | |
|---|---|---|
| 4,530,357 | 7/1985 | Pawloski et al. . |
| 4,600,007 | 7/1986 | Lahodny et al. ......................... 128/318 |
| 5,170,800 | 12/1992 | Smith et al. ............................. 128/751 |
| 5,176,699 | 1/1993 | Markham .................................. 606/207 |
| 5,254,129 | 10/1993 | Alexander ................................ 606/170 |
| 5,383,471 | 1/1995 | Funnell .................................... 128/751 |
| 5,395,375 | 3/1995 | Turkel et al. .............................. 606/83 |
| 5,489,292 | 2/1996 | Tovey et al. ............................. 606/207 |
| 5,626,609 | 5/1997 | Zvenyatsky et al. ................... 606/208 |
| 5,683,359 | 11/1997 | Farkas et al. .............................. 606/83 |
| 5,782,749 | 6/1998 | Riza ........................................ 600/117 |

FOREIGN PATENT DOCUMENTS

| | | |
|---|---|---|
| 0706780A2 | 4/1996 | European Pat. Off. . |
| WO 96/03926 | 2/1996 | WIPO . |

*Primary Examiner*—Gene Mancene
*Assistant Examiner*—Pedro Philogene
*Attorney, Agent, or Firm*—Nikaido Marmelstein Murray & Oram LLP

[57] ABSTRACT

A cutting device for cutting tissue is particularly useful during endoscopic knee surgery. The device includes first and second co-operating jaw parts which are operable to close together to cut an object placed therebetween and a gripping member for gripping the object to be cut during an earlier part of the jaw closing action thus preventing tissue slippage during cutting. A method of using the cutting device is also disclosed.

20 Claims, 2 Drawing Sheets

CUTTING DEVICE

FIELD OF THE INVENTION

This invention relates to a cutting device and, in particular, but not exclusively, to cutting device for cutting tissue during endoscopic surgery.

BACKGROUND OF THE INVENTION

Cutting devices have been developed which include loops for the finger and thumb of the endoscopic surgeon and an elongate stem secured to the first of the two loops at the other end of which stem is located the cutting head. A channel is usually located in the stem in which is located a wire connecting the second loop to a moveable jaw on the cutting head. The other jaw is generally fixed and formed by an aperture at the end of the stem located opposite the jaw connected to the wire. As with a pair of conventional scissors, movement of the loops away from or towards each other effects a corresponding movement in the cutting head at the end of the stem. In many surgical applications, a very small head is required for accurate cutting of body tissues. Unfortunately, there is the problem of slippage of the object being cut. This problem is caused, during surgery, because of the presence of bodily fluids reducing the friction between the cutting head and the tissue. The problem is particularly acute during endoscopic surgery because it is not possible to hold the tissue in the cutting head.

A head has been developed with a series of lateral grooves formed on the cutting face of the moving jaw which act to hold or grip the tissue during cutting. Unfortunately, it has been found that the grooves reduce the cutting efficiency of the jaw along its cutting edges. This is particularly the case when the cutting head is very small. A cutting head has been developed with straight cutting edges along either side and a planar face which is terminated by a sharp tooth at the end of the jaw. This has resulted in improved efficiency during cutting by increasing the cutting efficiency but the problem of slippage still remains.

Again, this is particularly a problem where a small cutting head is required in order to cut inaccessible areas during, for instance, endoscopic surgery. In such applications, the cutting head may need to be small in order to gain access to the tissue to be cut but the tissue area may be relatively large in proportion to the size of the cutting head. Thus, it is imperative that very little slippage occurs to reduce the cutting time to a minimum.

SUMMARY OF THE INVENTION

It is one of the objects of the embodiments of this invention to address the above problems.

According to a first aspect of the present invention there is provided a cutting device for cutting tissue during endoscopic surgery comprising first and second co-operating opposing jaw parts which are operable to close together to cut an object placed there between and a gripping member to grip the object during the initial part of the jaw closing action, wherein the gripping member extends from one of the jaw parts between the hinge and the front of the jaw substantially in the direction of the opposite jaw part so that material placed between the said jaws is held by the gripping member and prevented from sliding forward in the direction of the front of the jaw as the jaws close together, characterized in that only one said gripping member is provided between the hinge and the front of the jaw.

By minimizing the interruptions or serrations in the cutting edge, cutting efficiency is maximized while, at the same time, utilizing one gripping member to hold the tissue and prevent slippage during the cutting action.

Preferably, the only one said gripping member is located substantially midway between the front of the jaw and the hinge thereof.

In such a manner, by providing only one gripping member, the volume of material held between the jaws on the rearward side of the gripping member may be maximized.

Although, the midway position is preferred, the position is chosen so as to give high cutting efficiency, high volume of material and low tissue loss through slippage.

Preferably, the gripping member is formed by the internal surface of the jaws from which it depends in the form of a ridge thereon. Preferably, the ridge forming the gripping member has a concave rearward slope merging with the surface of the jaw.

Preferably, the gripping member extends laterally fully across the jaw part from which it depends.

Preferably, a further front gripping member is formed at the front of the jaw which may be on the same or the opposite jaw part.

By providing only one gripping member between the hinge and the front gripping member, slippage is reduced during cutting but reduced cutting efficiency, due to serrated cutting edges, is minimized. Furthermore, the presence of only one said gripping member maximises the "bite" of the jaw by increasing the volume of tissue which can be placed in the jaw and secured against slippage. This is improved if the angle of the plane of the face (or roof) of the jaw is greater between the hinge and the first gripping member than would be possible between the hinge and the front gripping member alone. This feature may also be present to a small extent on serrated jaws but here the advantage of the feature is not maximized as with a single additional gripping member which produces a relatively large volume for backfilling with tissue. Therefore, preferably, the angle of the plane of the inward face of the jaw from which the gripping member depends is greater between the hinge and the base of the gripping member than the corresponding angle between that gripping member and the front of the jaw.

Preferably, the gripping member is a sharp tooth which projects from the first or second co-operating jaw part. Preferably, the gripping member and the front gripping member project from the same jaw part.

Advantageously, the gripping member acts to grip the tissue during an earlier part of the closing or cutting action of the jaw and before closure of the jaw is complete and therefore reduces slippage of the tissue in the jaw prior to completion of the cut.

Preferably, only two teeth are provided on the first jaw part.

Typically, the second jaw is formed into an aperture the inner walls of which are designed to be close fitting with the outer walls of the first jaw.

Preferably, the lower edges of the outer walls of the first jaw and the upper edges of the inner walls of the second jaw form cutting edges.

Preferably, the front gripping member and the gripping member comprise a first and second tooth.

Preferably, the profile of the cutting edge of the first jaw is substantially straight from the crotch of the jaw to the base region of the second tooth and from the second tooth to the first tooth. However, the cutting edge, preferably, curves concavely from the base region of the second and first tooth to the apex of the respective tooth.

During use, the open jaws are placed over the tissue to be cut and thereafter closed causing the gripping member to bite into the tissue to prevent it squeezing out of the jaw during all or the remainder of the closing action.

Advantageously, the use of only two teeth renders the device easier to manufacture than one with a large number of teeth which is especially important when the jaws are very small which is common in many surgical applications. Furthermore, the use of a small number of teeth increases cutting efficiency by increasing the force applied at the tooth head and not spreading the load over a larger number of teeth. In addition, the cutting edge performs the cutting action from the crotch outwards and a larger number of teeth would interfere with the smoothness and efficiency of the cutting action found where a substantially straight cutting edge is applied.

In addition, preferably, the gripping members act as cutting edges during the cutting action. Thus, where the gripping members are formed as teeth, the gripping edge of each tooth is sharpened. As the gripping member projects from the interior face of the jaw it comes into cutting contact with the tissue to be cut prior to the cutting edges which precede it in the direction of the crotch. Accordingly, by spacing the two teeth in this manner no slippage of tissue will occur during the cutting action. It is preferred that the depth of the gripping member from the face of the jaw and its respective cutting edges is such that the edge of the tooth will come into contact with the tissue prior to the cutting edges which precede it, as far as the preceding gripping member in the direction of the crotch or, in the case of the gripping member nearest to the crotch as far as the crotch itself.

Preferably, the device is operated by hand.

Preferably, the second jaw part is formed into an appropriately sized cavity having cutting edges on its cutting side and the first jaw part forms a pivoting insertion which also has cutting edges on its cutting side. The first jaw part, preferably, pivots about a pivot located behind the cutting surfaces from an open position where the cutting edges form a "V" shaped opening to a closed position where the insertion is located within the walls of the aperture.

In a preferred embodiment, the pivoting/cutting action is effected by a thumb and finger loop which are moved apart altogether to effect a corresponding movement in the jaw parts.

Typically, one jaw part and its corresponding loop are fixed in relation to each other and the second jaw part and its loop are pivotable with respect to each other. Turning to a preferred embodiment, the jaw parts are located at one end of an elongate stem which extends from the housing around the pivot between the two loop ends and which is formed into an aperture at its remote end with cutting edges on the walls of the aperture. The aperture forms the second jaw part and is designed to be close fitting with the outside walls of an insertable first jaw part which has corresponding cutting edges which are designed to overlap with the cutting edges of the aperture to effect the cutting action. The first jaw part is pivotable about a bar which extends laterally across the aperture. A wire connects the pivotable first jaw part to its respective loop so that pivoting of the loop causes corresponding pivoting of the first jaw part.

Preferably, the edge of the gripping member is substantially perpendicular to the tissue to be cut at the point of contact. Preferably, the edge profile of the end tooth matches the profile of the end of the aperture and may be curved.

The invention may be used with any surgical cutting implement and the cutting head is not limited in size but may be utilized for any size of cutting head.

According to a second aspect of the present invention there is a provided a method of cutting body tissue using a cutting device according to the first or third aspect of the present invention which includes the steps of:
(a) placing the open jaws of the cutting device over the tissue to be cut,
(b) closing the jaws of the cutting device until the gripping member is urged into the tissue to prevent the tissue sliding forward in the jaw, and
(c) continuing the closing action to cut the tissue thus held.

According to a third aspect of the present invention there is provided a cutting device for cutting tissue during endoscopic surgery comprising first and second cooperating jaw parts which are operable to close together to cut an object placed therebetween characterised in that a single gripping member is provided between the hinge and the front of the jaw to grip the object prior to cutting of the tissue.

Preferably, the object to be cut is animal or human tissue.

Preferably, a further gripping member is provided for gripping the tissue during the cutting action.

The invention according to either the second or third aspect may incorporate any one or more of the features of the invention detailed in relation to the first aspect of the invention with the front gripping member of the first aspect and its parts replacing the further gripping member of the third aspect.

By gripping the tissue prior to cutting, in accordance with the third aspect of the invention, it may be possible to dispense with the further gripping member. Nevertheless, the further grip is preferred in order to avoid any tissue slippage during the latter part of the closing action.

BRIEF DESCRIPTION OF THE DRAWINGS

An embodiment of the invention will now be described, by way of example, with reference to the accompanying drawings in which.

DESCRIPTION OF THE PREFERRED EMBODIMENTS

Figure 1A:
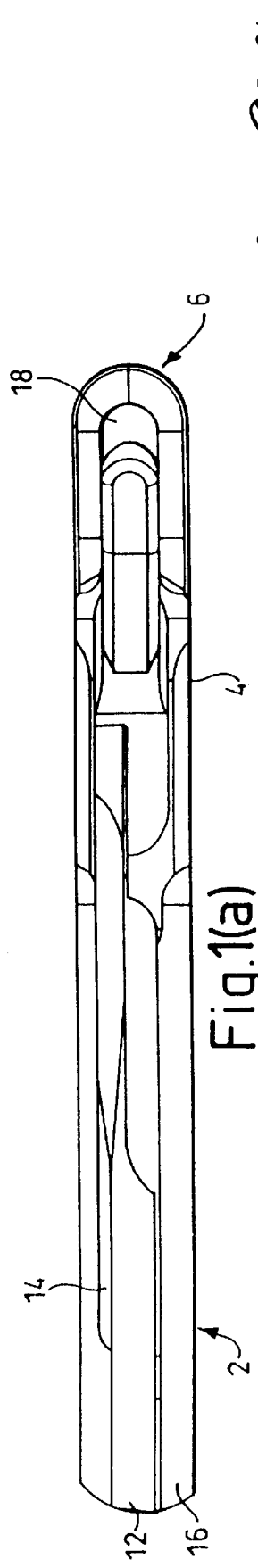
FIG. 1a shows a plan view of a cutting device according to the present invention with the jaws in the open position.
Figure 1B:
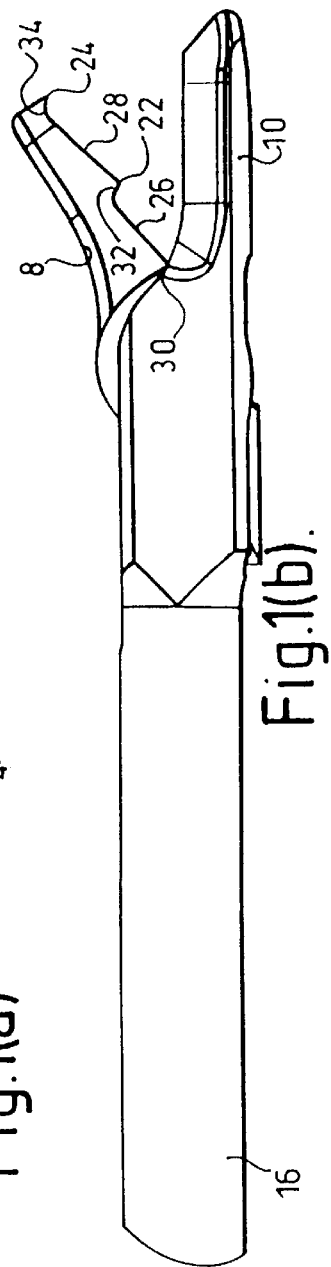
FIG. 1b shows a side view of a cutting device according to the present invention with the jaws open.
Figure 1C:
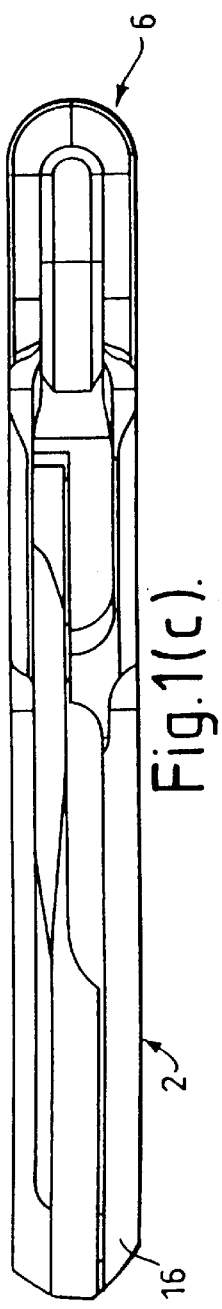
FIG. 1c shows a plan view of a cutting device according to the present invention with the jaws closed.
Figure 1D:
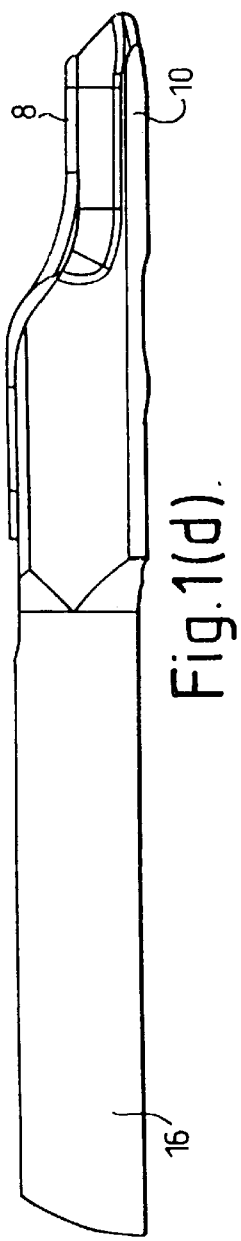
FIG. 1d shows a side view of a cutting device according to the present invention with the jaws closed.
Figure 2:
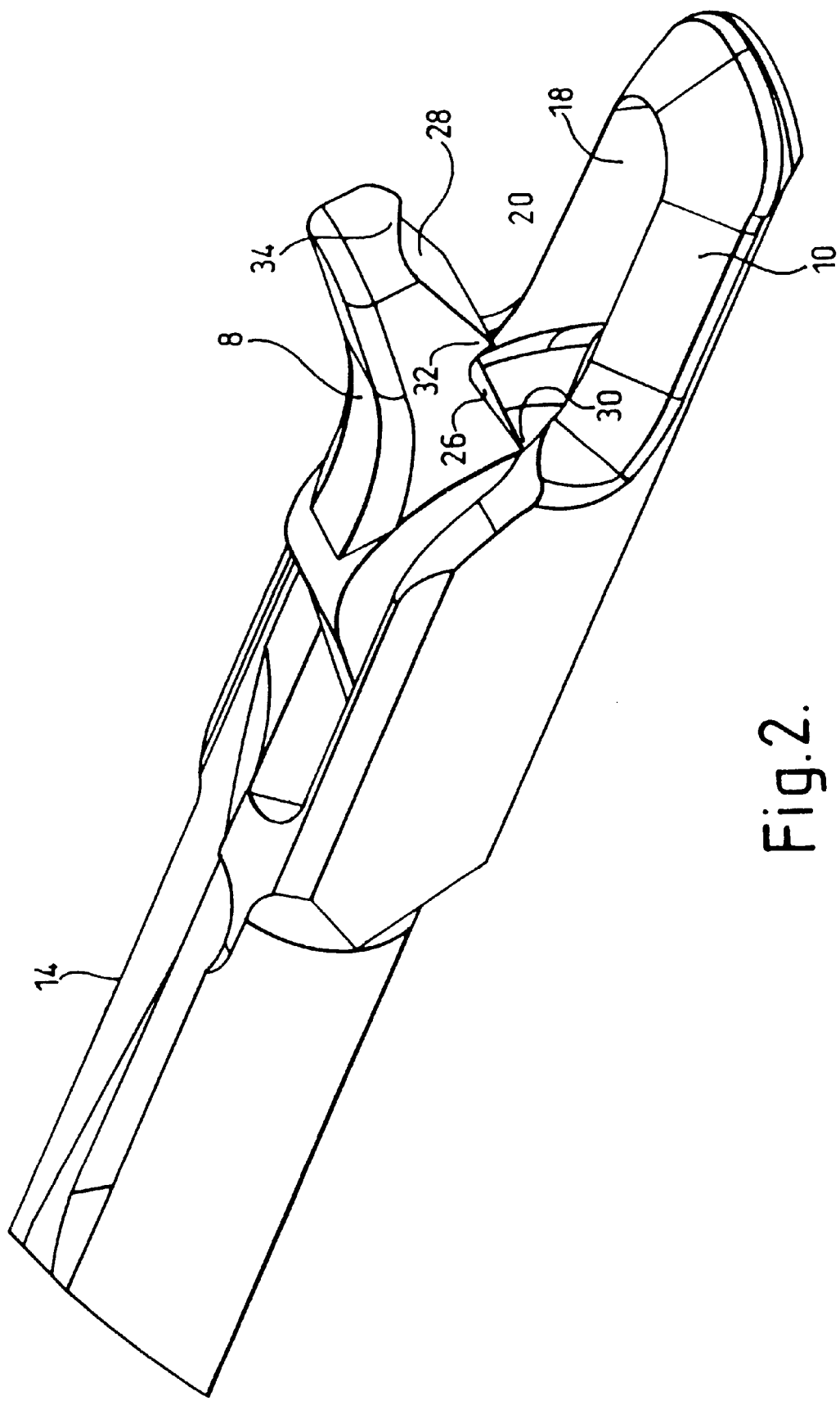
FIG. 2 shows a prospective view of a cutting device according to the present invention.

Referring to FIG. 1a, a cutting device 2 is shown partially. The cutting device 2 has a cutting head 4 which incorporates a set of jaws 6 which set includes a pivotable jaw 8 and a fixed jaw 10. The pivotable jaw 8 is connected to a wire 12 which is slidably located in a "U" shaped channel 14 formed in the stem 16. The lower jaw 10 is integral with the stem 16 and includes a centrally disclosed aperture 18 which is designed to be close fitting with the pivotable jaw 8 which resides therein in the closed position. The upper edges of the fixed jaw 10 formed by the walls of the aperture 18 provide a cutting edge for the lower jaw 10. The lower surface 20 of the pivotable jaw 8 is shaped so as to provide two spaced lateral gripping edges 22, 24, a curved edge 24 at the front of the jaw and a straight edge 22 approximately mid way along the length of the jaw 8. Each edge 22, 24 is preceded by a substantially planar surface 26, 28 which, in the first case, extends from the crotch 30 of the set of jaws 6 to the hilt of the first gripping member 32 and, in the second case, from the point of the cutting edge 22 to the hilt of the second gripping member 34. The respective edges 22,24 of the gripping members 32, 34 terminate a smooth concavely shaped ridge which rises from the respective planar surface 26,28 which precedes it. A lateral bar (not shown) locates the pivotable jaw 8 in the aperture 18 and causes it to pivot thereover in response to longitudinal movements of the wire 12 with respect to the stem 16. The wire 12 is fixed to the pivotable jaw 8 in such a manner that a rearward movement of the wire with respect to the cutting head causes the jaw to open and a forward movement of the wire with respect to the cutting head causes the jaw to close.

In use, the cutting device is employed in a similar manner to a pair of scissors. The surgeon simply opens the gap between the thumb and index finger loops thereby widening the distance between the finger loops and simultaneously opening the jaws of the cutting head. Thereafter, using an endoscope, the jaws may be placed over the tissue to be cut and closed thereover to effect cutting. As the jaws close over the tissue the rear gripping edge bites into the tissue to prevent the tissue travelling forward in the jaw. In this manner, the cutting head closes over the area of tissue intended by the surgeon leading to greater precision and accuracy in the operation. Such precision reduces operating time and gives a greater likelihood of success in the operation. The concave rear surface of the gripping member allows a build up of tissue behind the rear grip with is caused by the closure of the jaw. A straight or convexed rear surface would tend to push the tissue back into the crotch of the jaw which would prevent smooth cutting. Thus, it is preferred that one or each gripping member is preceded by a substantially concave surface.

The manufacture of the cutting head is relatively simple compared to the multi ridged grip. This allows accurate machining of the cutting head for precise application where the size of the cutting head must, by nature of the operation, be very small. The greater complexity of the jaw surface on the multi ridged cutting head renders its manufacture difficult in such small head applications. In addition, the invention provides a continuous cutting edge and the concave surface introduces a gentler transition from the straight cutting edge to the edge of the rear grip which provides a smoother cutting action. The "V" shaped ridges of the multi ridged jaw decrease the efficiency of the cut which causes the tissue to "jam" and may cause the surgeon to close the head over the tissue several times before the tissue is actually cut. Such a technique also leads to tearing of the tissue as well as an increase in operation time. By only providing two gripping edges, the invention maintains a high pressure per gripping edge during the cutting operation which maintains the efficiency of the cut while, at the same time, preventing slippage of the tissue out of the jaw prior to cutting. Nevertheless, it is envisaged that more than two gripping members could be used per cutting head and, in general, the number of gripping members would be the best balance between tissue slippage and cutting efficiency and would to some extent depend upon the size of cutting head required for each particular surgical application.

A cutting device as defined above should be of considerable benefit in surgery and with addition to the benefits listed in the foregoing description it should be mentioned that in endoscopic surgery one is often maneuvering in tight places. Therefore opening the jaw is restricted by the structures around it, to get more tissue in the jaw you would normally have to open the jaws further. The double tooth creates a bigger opening (gap) whilst not having to physically open the jaws further. This is a major benefit over straight or serrated jaws.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

I claim:

1. A cutting device for cutting tissue during endoscopic surgery comprising:

first and second co-operating opposed jaw parts which are operable to close together to cut an object placed there between; and a gripping member to grip the object during an initial part of a jaw closing action, wherein the gripping member extends from one of the jaw parts, between a hinge and a front of the jaw parts, substantially in a direction of an opposite jaw part so that material placed between said jaw parts is held by the gripping member and prevented from sliding forward in a direction of the front of the jaw parts as the jaw parts close together, and wherein only one said gripping member is provided between the hinge and the front of the jaw parts.

2. A cutting device according to claim 1, wherein the gripping member is located substantially midway between the front of the jaw parts and the hinge.

3. A cutting device according to claim 1, wherein a front gripping member is formed at the front of the jaw parts which is on one of the same and the opposite jaw part.

4. A cutting device according to claim 1, wherein the gripping member is a sharp tooth which projects from one of the first and second co-operating opposed jaw parts.

5. A cutting device according to claim 3, wherein both the gripping members and the front gripping member project from the same jaw part.

6. A cutting device according to claim 1, wherein the second jar part is formed having an aperture, inner walls of the aperture are designed to be close fitting with outer walls of the first jaw part.

7. A cutting device according to claim 1, wherein lower edges of outer walls of the first jaw part and upper edges of inner walls of the second jaw part form cutting edges.

8. A cutting device according to claim 7, wherein a profile of the cutting edge of the first jaw part is substantially straight from the hinge of the jaw parts to a base region of the gripping member and from an apex of the gripping member to a front gripping member.

9. A cutting device according to claim 7, wherein the cutting edge curves concavely from a base region of the gripping member to an apex of the gripping member.

10. A cutting device according to claim 3, wherein at least one of the gripping members also act as cutting edges during the cutting action.

11. A cutting device according to claim 1, wherein a depth of the gripping member from an internal face of the jaw part and respective cutting edges is such that the edge of the gripping member will come into contact with the tissue prior to the cutting edges.

12. A cutting device according to claim 1, wherein the device is designed to be operated by hand.

13. A cutting device according to claim 1, wherein the second jaw part is formed into an appropriately sized cavity having cutting edges on a cutting side and the first jaw part forms a pivoting insertion which also has cutting edges on a cutting side.

14. A cutting device according to claim 1, wherein the first jaw part pivots about a pivot located behind cutting surfaces from an open position where cutting edges form a "V" shaped opening to a closed position where the first jaws part is located within walls of an aperture.

15. A cutting device according to claim 1, adapted to be used with any surgical cutting implement.

16. A cutting device for cutting tissue during endoscopic surgery comprising:

first and second co-operating jaw parts which are operable to close together to cut an object placed therebetween; and a single gripping member is provided between a hinge and a front of the jaw parts to grip the object prior to cutting of the tissue.

17. A cutting device according to claim 16, wherein the object to be cut is animal or human tissue.

18. A cutting device according to claim 16, wherein a further gripping member is provided for gripping the tissue during the cutting action.

19. A cutting device according to claim 16, wherein the gripping member is located substantially midway between the front of the jaw parts and the hinge.

20. A method of cutting body tissue using a cutting device comprising the steps of:

(a) placing the open jaw parts of the cutting device over the tissue to be cut, (b) closing the jaw parts of the cutting device until a gripping member is urged into the tissue to prevent the tissue sliding forward in the jaw parts, wherein only one said gripping member is provided between a hinge and a front of the jaw parts, and (c) continuing the closing action to cut the tissue thus held.

* * * * *